(12) United States Patent
Heuscher et al.

(10) Patent No.: US 7,835,488 B2
(45) Date of Patent: Nov. 16, 2010

(54) SWEPT ANNODE CT SCANNER

(75) Inventors: Dominic J. Heuscher, Aurora, OH (US); Randall P. Luhta, Highland Heights, OH (US); Marc A. Chappo, Elyria, OH (US); Rainer Pietig, Herzogenrath (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 36 days.

(21) Appl. No.: 12/446,765

(22) PCT Filed: Oct. 16, 2007

(86) PCT No.: PCT/US2007/081467

§ 371 (c)(1),
(2), (4) Date: Apr. 23, 2009

(87) PCT Pub. No.: WO2008/115275

PCT Pub. Date: Sep. 25, 2008

(65) Prior Publication Data

US 2010/0040194 A1     Feb. 18, 2010

Related U.S. Application Data

(60) Provisional application No. 60/863,646, filed on Oct. 31, 2006.

(51) Int. Cl.
A61B 6/03 (2006.01)

(52) U.S. Cl. ...................................... 378/11

(58) Field of Classification Search .................. 378/4, 378/9, 11, 19, 16, 124, 136, 137
See application file for complete search history.

(56) References Cited

U.S. PATENT DOCUMENTS

| 4,352,021 | A | 9/1982 | Boyd et al. |
| 4,914,681 | A | 4/1990 | Klingenbeck |
| 7,023,950 | B1 | 4/2006 | Annis |
| 2004/0258196 | A1 | 12/2004 | Lounsberry |
| 2004/0264626 | A1 | 12/2004 | Besson |
| 2005/0100127 | A1 | 5/2005 | Zhao et al. |
| 2006/0002514 | A1 | 1/2006 | Dunham |
| 2006/0002515 | A1 | 1/2006 | Huber et al. |

FOREIGN PATENT DOCUMENTS

| EP | 0269927 A1 | 6/1988 |
| GB | 2255887 A | 11/1992 |
| WO | 2004072679 A2 | 8/2004 |

*Primary Examiner*—Irakli Kiknadze

(57) ABSTRACT

A computed tomography method includes rotating an electron beam along an anode (104) disposed about an examination region (112) for a plurality of sampling intervals in which x-ray projections are sampled. The electron beam is swept during each sampling interval to generate a plurality of successive focal spots at different focal spot locations during each sampling interval, wherein the focal spots generated in a given sampling interval include a sub-set of the focal spots generated in a previous sampling interval. The x-ray projections radiated from each of the plurality of focal spots is sampled during each sampling interval. The resulting data is reconstructed to generate volumetric image data.

23 Claims, 7 Drawing Sheets

SWEPT ANNODE CT SCANNER

CROSS REFERENCE TO RELATED APPLICATIONS

This application claims the benefit of U.S. provisional application Ser. No. 60/863,646 filed Oct. 31, 2006, which is incorporated herein by reference.

The present application generally relates to imaging systems. It finds particular application to computed tomography (CT) and, more particularly, to a system and method for generating and detecting x-ray radiation.

Conventional cone beam CT scanners have included an x-ray tube with a cathode and an anode disk. In general, the x-ray tube rotates about an examination region. While rotating as such, the cathode emits an electron beam that strikes the anode disk to produce a source of radiation or focal spot. The anode disk typically rotates with respect to the electron beam and dissipates heat generated during the x-ray generation. The resulting radiation traverses an object within the examination region and illuminates at least one detector. The detector generates projection data indicative of the detected radiation, and the projection data is reconstructed to generate volumetric image data of the object.

It is often desirable to acquire relatively high temporal resolution data with such a system. For example, high temporal resolution data is often desired when scanning moving objects such as when performing a cardiac CT scan. In one instance, higher temporal resolution data is obtained by increasing x-ray tube rotation speed. However, with this approach less x-rays or x-ray flux is detected during each data acquisition interval, which may result in degraded photon statistics and image quality. In addition, the speed at which an x-ray tube can be rotated about the examination region is mechanically limited. In order to compensate for the reduced x-ray flux and improve image quality, tube power has to be increased during such a scan.

However, the power output by conventional x-ray tubes has been limited. One factor that limits the power output is the relatively large temperature increase as the rotating anode is struck by the electron beam. The temperature of a focal spot position is a function of, among other things, the amount of time the electron beam passes over the focal spot width. This time is inversely related to the anode rotational speed, which is again mechanically limited. As a result, commercially available rotating anode x-ray tubes have typically been limited to about one hundred (100) kilowatts (kW) of electron beam power.

Aspects of the present application address the above-referenced matters and others.

In one aspect, a computed tomography method includes rotating an electron beam along an anode disposed about an examination region for a plurality of sampling intervals in which x-ray projections are sampled. The electron beam is swept during each sampling interval to generate a plurality of successive focal spots at different focal spot locations during each sampling interval, wherein the focal spots generated in a given sampling interval include a sub-set of the focal spots generated in a previous sampling interval. The x-ray projections radiated from each of the plurality of focal spots is sampled during each sampling interval. The resulting data is reconstructed to generate volumetric image data.

In another aspect, a computed tomography system includes an electron beam source that rotates and sweeps an electron beam along a ring-shaped anode for a plurality of sampling intervals in which x-ray projections are detected. The electron beam is swept during each sampling interval to generate a plurality of focal spots at different focal spot locations and successive sweeps partially overlap. A detector array samples x-ray projections radiated from each of the plurality of focal spots that traverse an examination region for each sampling interval. A reconstructor reconstructs the x-ray projections to generate volumetric image data.

In another aspect, a computed tomography system includes a ring-shaped anode that surrounds an examination region. A cathode rotates along the anode and repetitively sweeps an electron beam through a moving sweep window covering a plurality of focal spot locations to repeatedly generate a plurality of focal spots one after another at different focal spot locations as the cathode rotates around the examination region. The moving sweep window moves so that at least one similar focal spot is generated during two consecutive electron beam sweeps. A detector array detects x-rays emitted from each focal spot and generates signals indicative thereof. A combiner combines signals corresponding to x-rays that traversed a substantially similar path through the examination region. A reconstructor reconstructs the signals to generate volumetric image data.

The invention may take form in various components and arrangements of components, and in various steps and arrangements of steps. The drawings are only for purposes of illustrating the preferred embodiments and are not to be construed as limiting the invention.

Figure 9:
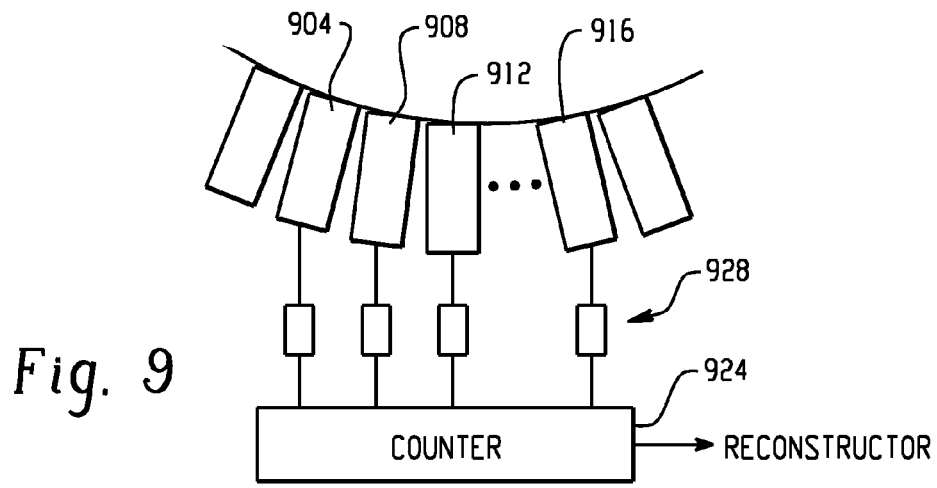
Figure 10:
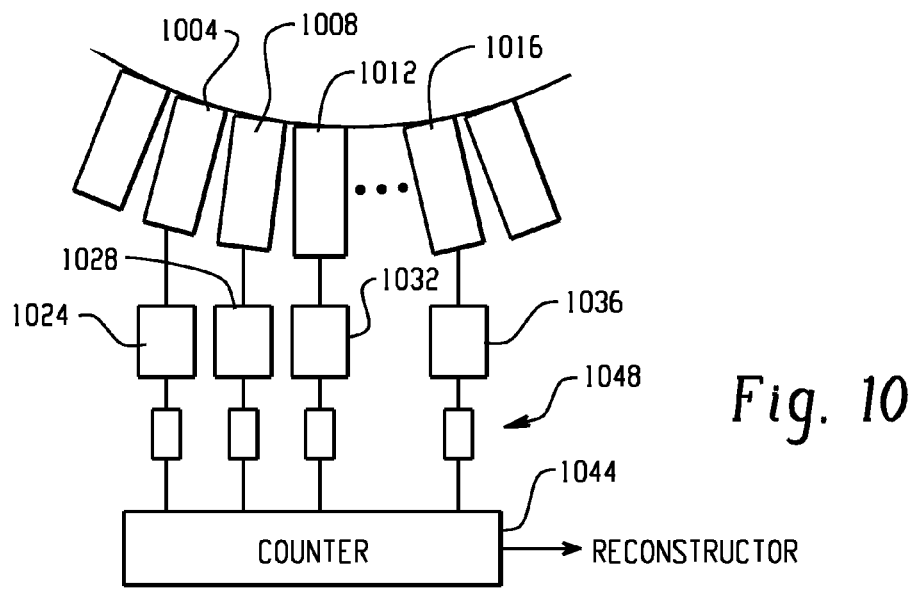
Figure 11:
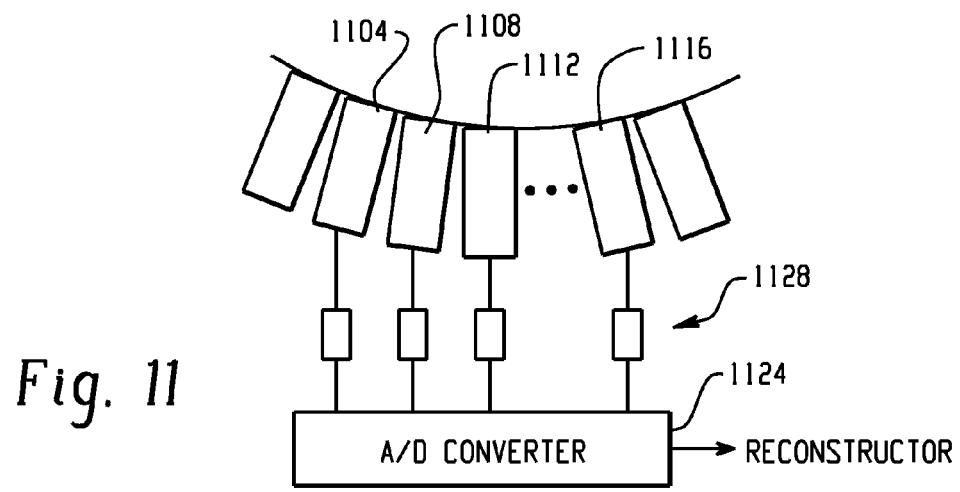

FIGS. 9, 10, and 11 illustrates exemplary data combining systems.

Figure 12:
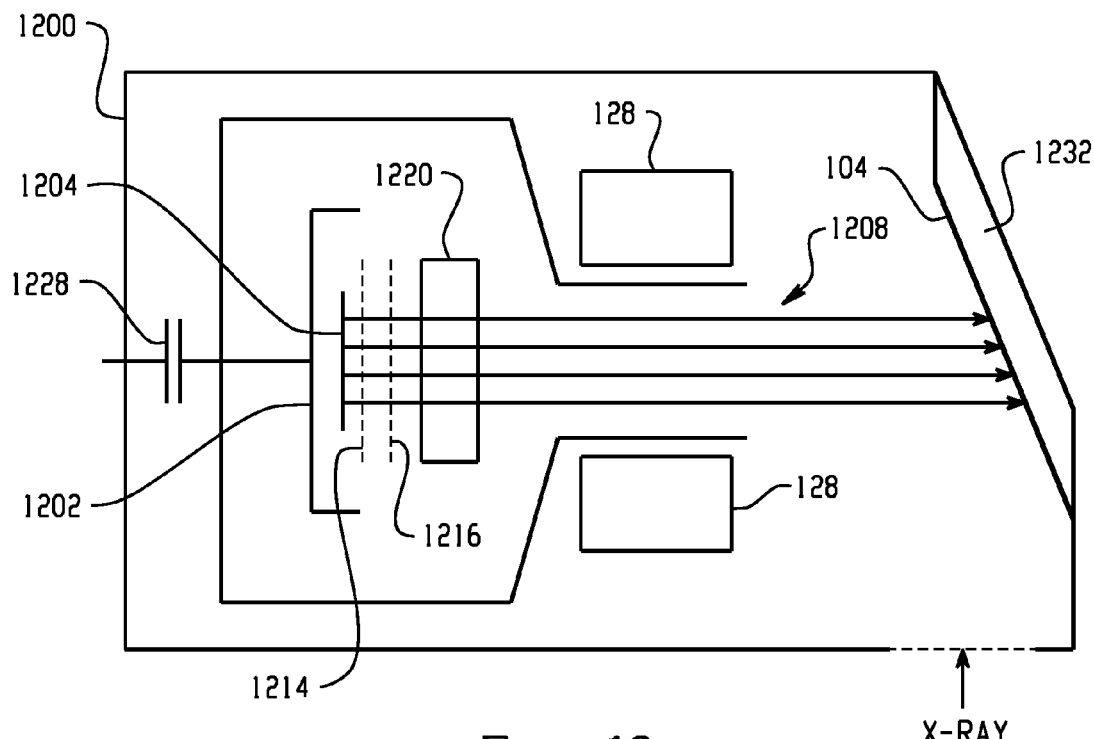

FIG. 12 illustrates an exemplary cathode/anode system.

Figure 13:
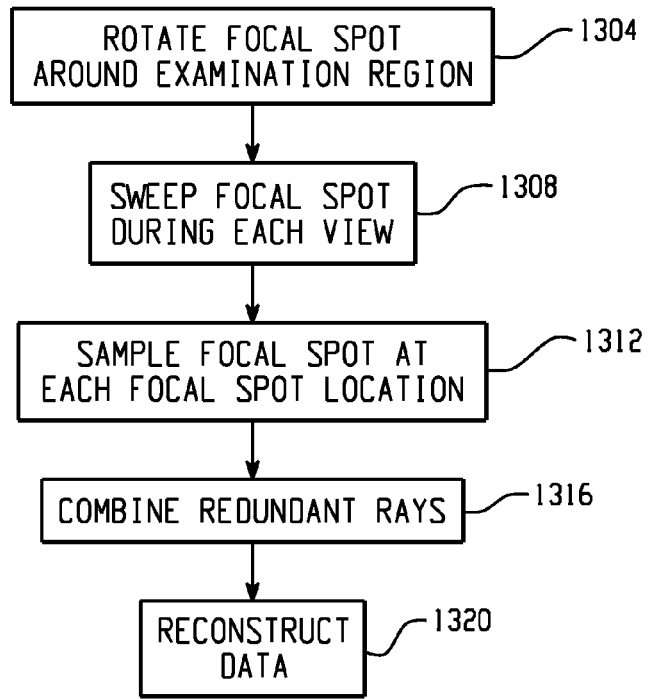

FIG. 13 illustrates an exemplary method.

Figure 1:
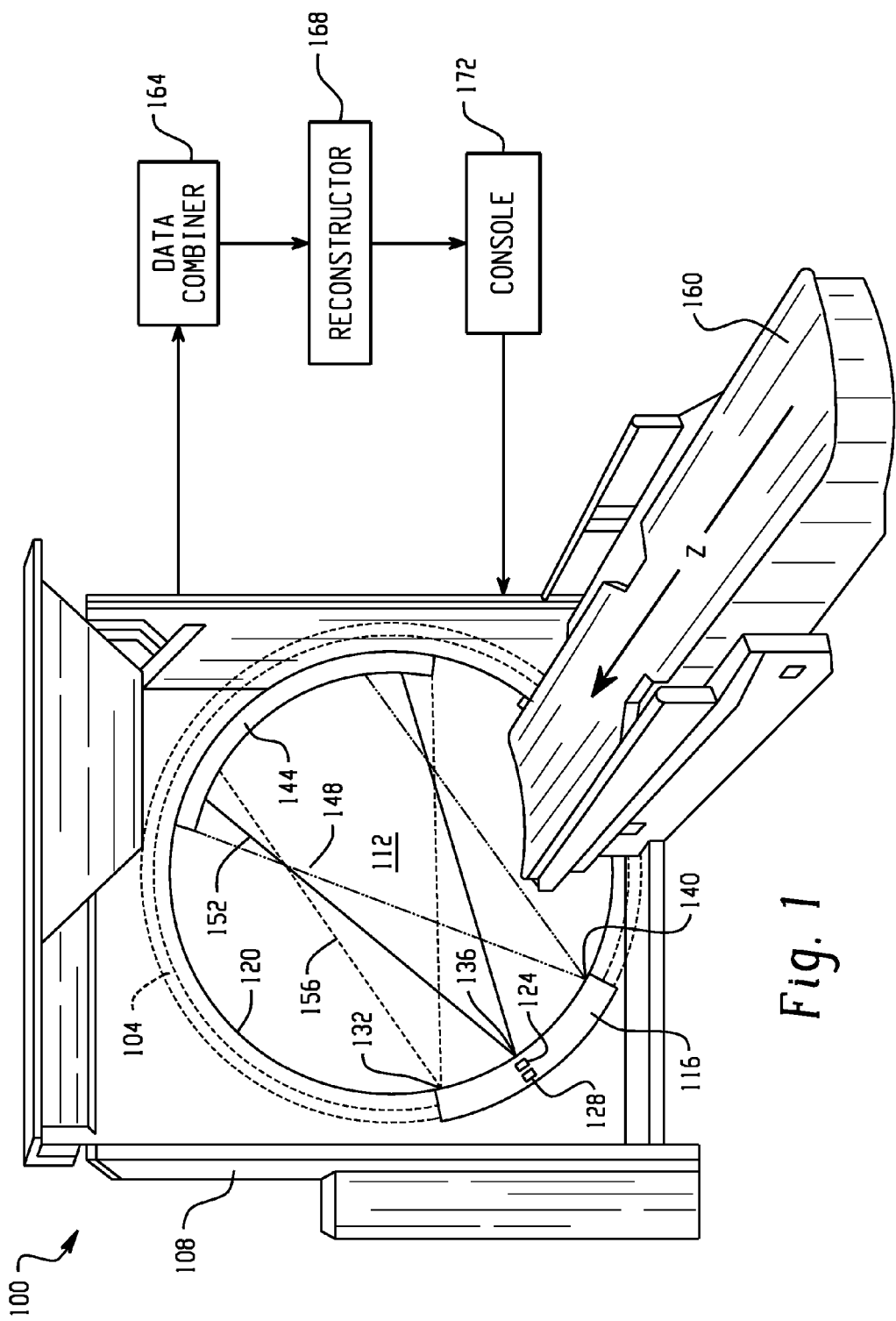
FIG. 1 illustrates an exemplary imaging system.
Figure 2:
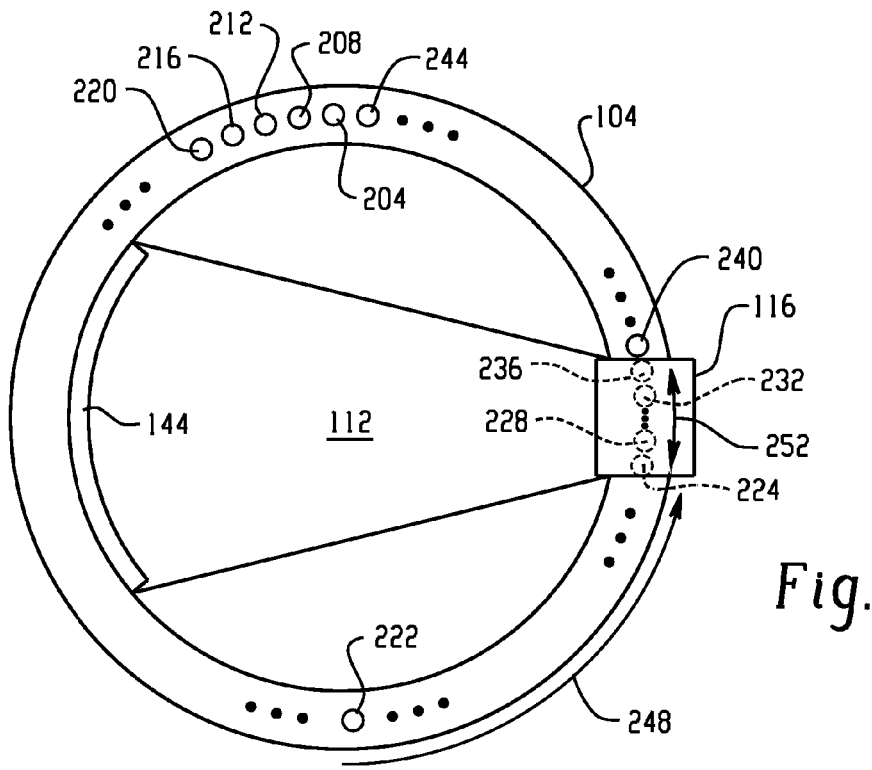
FIGS. 2-5 illustrate an exemplary technique for sweeping a focal spot.

With reference to FIG. 1, an imaging system 100 includes at least one generally annular or ring-shaped anode 104 disposed within a gantry 108 to surround an examination region 112. The anode 104 is stationary in that it does not rotate about the examination region 112. The system also includes a rotating gantry portion or member 120 which rotates about a longitudinal or z-axis.

A cathode 116 is positioned next to the anode 104 and offset therefrom in a longitudinal direction. The cathode 116 rotates along the anode 104 and around the examination region 112 via the rotating member 120. During scanning, the cathode 116 rotates as such for a plurality of views or angular sampling intervals in which x-ray projections are radiated and sampled.

The cathode 116 emits an electron beam that strikes the anode 104 to generate a focal spot (or a source of an x-ray projection) at the location on the anode 104 struck by the electron beam. In this example, the electron beam is pulsed, for example, turned "on" for a first time period and substantially turned "off" for another time period. A steering grid 124 pulses the electron beam to generate each focal spot. A beam focusing and deflection unit 128 directs the pulsed electron beam toward the anode 104. For instance, the unit 128 angularly sweeps or moves the pulsed beam along the anode 104.

In one implementation, the system 100 is configured so that the pulsing and sweeping of the electron beam is coordinated with the rotation of the cathode 116 about the z-axis. In this implementation, the electron beam is pulsed a plurality of times during a view to generate a plurality of focal spots within that view. Concurrently, the electron beam is swept so that these focal spots are generated one after another at different angular positions on the anode 104. By way of example, the illustrated embodiment shows a superposition of focal spots 132, 136, and 140 generated by sweeping the pulsed electron beam during the same view.

While the cathode 116 moves through a next contiguous view, the electron beam is again pulsed a plurality of times and swept to generate a plurality of focal spots at different angular positions on the anode 104. The system 100 is configured so that during a given view a subset of the focal spots generated during the previous view are generated again as described in greater detail below. As a result, each focal spot and, thus, the x-ray projections therefrom are generated during more than one view.

The rotating member 120 also supports an x-ray sensitive detector array 144 that subtends an angular arc opposite the cathode 116. In the illustrated embodiment, the detector array 144 rotates in coordination with the cathode 116 in a third generation configuration. The above described electron beam sweeping allows the cathode 116 and detector array 144 to rotate at about the same speed or more slowly, if desired, (compared to a configuration in which the beam is not swept) to reduce anode heat, which allows the applied power to be increased to improve photon statistics, or image quality.

The detector array 144 includes one or more multi-slice detectors having detector elements in both the longitudinal or z-axis direction and a transverse direction. Each detector element generates projection data indicative of the radiation it detects. The detector array 144 is configured with a suitable number of detector elements in the transverse direction so that the x-rays projections radiating from the different focal spot positions within a view are detected by the detector array 144 during that view. By way of example, the illustrated detector array 144 is configured so that each of the x-ray projections 148, 152, and 156 from the focal spots 132, 136, and 140, respectively, illuminates a sub-set of the detector elements during the illustrated view.

Since each focal spot is generated during multiple views, each focal spot is sampled during multiple views. As a result, an x-ray path through the examination region 112 is sampled during more than one view. By sampling the x-ray projection path during more than one view, the sampling time during each view can be reduced, while maintaining aggregate sampling time for each x-ray projection.

The redundant samples are conveyed to a data combiner 164, which combines projection data acquired along the same or similar paths, if desired, as described in greater detail below. The resulting data is conveyed to a reconstructor 168, which reconstructs this data using known algorithms such as, but not limited to, the FDK and Axial Wedge algorithms to generate volumetric image data. The image data is processed to generate one or more images of the scanned region of interest or a subset thereof.

The system 100 further includes a couch or patient support 160 that supports a subject such as a human within the examination region 112. The couch 160 is movable along the z-axis, the x-axis, and a y-axis. Such movement is used to guide a subject within the examination region 112 before, during, and after scanning.

An operator console 172 facilitates user interaction with the scanner 100. Software applications executed by the console 172 provide the user with an interface for configuring and/or controlling operation of the scanner 100. For instance, the user can interact with the operator console 172 to select a scan protocol, change scan parameters, initiate, pause and terminate scanning, etc. The console 172 also is used to view images, manipulate data, measure various characteristics of the data (e.g., CT number and noise), etc.

By rotating and sweeping the focal spot as described above to generate each focal spot in more than one view, the time interval in which a focal spot is generated in each view can be reduced. By way of non-limiting example, instead of generating a focal spot in a single view for a time period K, the focal spot may be generated in M views for a time period of K/M or some other fraction of the time K in each view. In this manner, the focal spot is still aggregately generated for the time period K. However, reducing the time period in which the focal spot is generated in each view reduces the temperature increase at the focal spot location on the anode 104. As a result, the amount of power that can be applied to the anode 104 at each focal spot during each view increases relative to a configuration in which the electron beam is not swept as such. In one instance, this is leveraged when performing high temporal resolution scans. For example, the tube power can be increased relative to conventional scanning techniques to increase the photon flux to increase or obtain a desired image quality.

FIGS. 2, 3, 4, and 5 illustrate an exemplary approach for rotating and sweeping the electron beam during each view. Initially referring to FIG. 2, the anode 104 is shown as having a plurality of focal spot locations 204, 208, 212, 216, 220, . . . , 222, . . . , 224, 228, . . . , 232, 236, 240, . . . , and 244. The cathode 116 is angularly positioned at a start angle 248, which in this example is referenced from a focal spot position 222 on the anode 104. The start angle 248 is the angular position of the first focal spot location (the focal spot location 224 in the illustration) that will be generated during a sweep of the electron beam within a sweep angle 252.

The sweep angle 252 is determined based on the number of views, the sampling interval during each view, and the rotation time of the cathode 116 about the examination region 112. For example, in one instance a sweep angle of sixty-one and seven tenths (61.7) degrees corresponds to a configuration having one thousand eighty (1080) views, a one (1) microsecond (µs) sampling interval, and a two-hundred (200) millisecond (ms) rotation time. With this configuration, there generally are two hundred (200) focal spot positions within a single sweep. If each view is offset from a previous view by one (1) focal spot location, the system would have one thousand eighty (1080) views. The sweep speed of the electron beam through the sweep angle 252 during each view is about three (3) kilometers per second (km/s).

Figure 3:
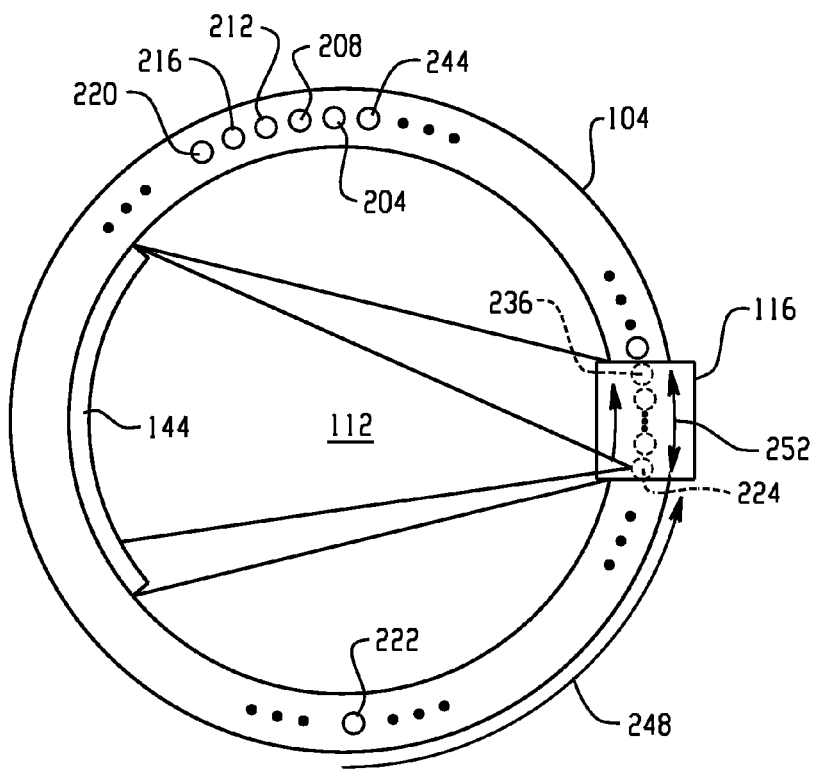
Figure 4:
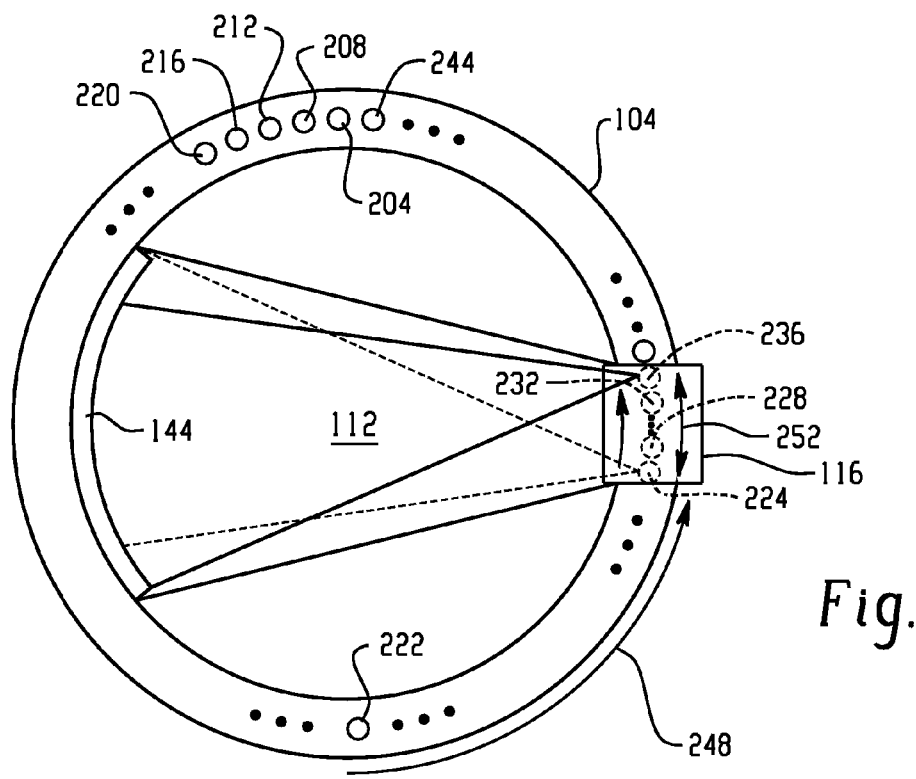

FIGS. 3 and 4 show the pulsed electron beam being swept beginning at the first focal spot location 224 through the sweep angle 252 to successively generate focal spots at focal spot locations 224, 228, . . . , 232, and 236 within the sweep angle 252. Upon generating and sampling the x-ray projection data radiated from the focal spot locations 224-236, the cathode 116 and the detector array 144 have angularly moved to a next view position as shown in FIG. 5.

Figure 5:
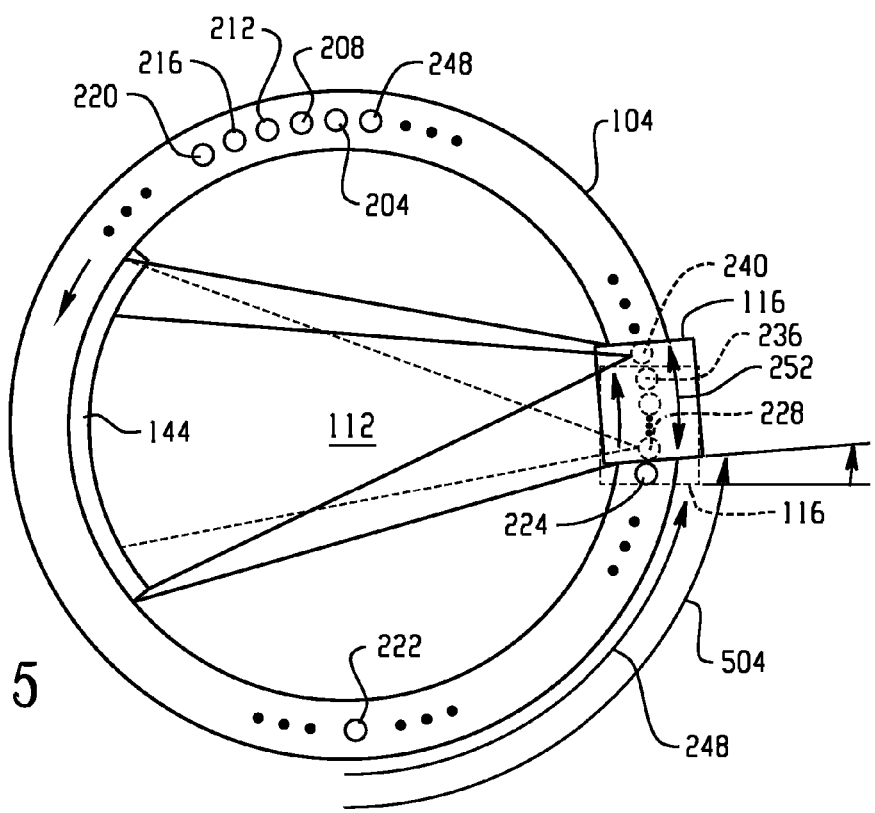

In FIG. 5, the next view angular position is shifted by one focal spot location. As a result, the electron beam is again swept through the sweep angle 252 at a next start angle 504, beginning at the focal spot location 228. Likewise, the cathode 120 and the detector array 144 rotate through this view, and each of the focal spots at the locations 228-244 is generated and sampled one after another. The above is repeated for each angular view as the cathode 116 rotates around the z-axis.

Using the above approach, during each view that is sampled the electron beam is angularly swept along the anode 104 in a direction of the rotation of the cathode 116 beginning at a different start angle. Sweeping the electron beam as such sweeps the focal spot from a first or initial focal spot location within the sweep angle 252 to a last focal spot location within the sweep angle 252, wherein one or more other focal spot locations are located between the first and last focal spot locations. For a subsequent view, the electron beam is again swept along the anode 104 beginning with a first focal spot location within the sweep angle 252. The first focal spot location is incremented by at least one focal spot location in the direction of the rotation of the cathode 116 relative to the previous view.

As described previously, rotating and sweeping the electron beam as such generates each focal spot in more than one view so that the amount of time in which the focal spot is generated in each view is reduced. This in turn reduces the temperature increase on a focal spot location as the electron beam passes over that focal spot for a given instantaneous heat dissipation of the anode 104. This can be seen from Equation 1 which estimates the temperature at a focal spot location.

$$T = \frac{2P}{A} \sqrt{\frac{t}{\pi \lambda c_V}},$$ Equation 1 wherein P represents the power delivered to the anode (which is about 60% of the electron beam power), A represents the focus area, $\lambda$ represents the heat conduction coefficient, $c_v$ represents the specific heat capacity per volume of the focal track material, and t is the amount of time the electron beam passes a focal spot. From this equation, reducing the spot time (t) reduces the focal spot location temperature (T), and allows the power delivered to the anode 104 (P) to be increased for a given temperature (T).

Figure 6:
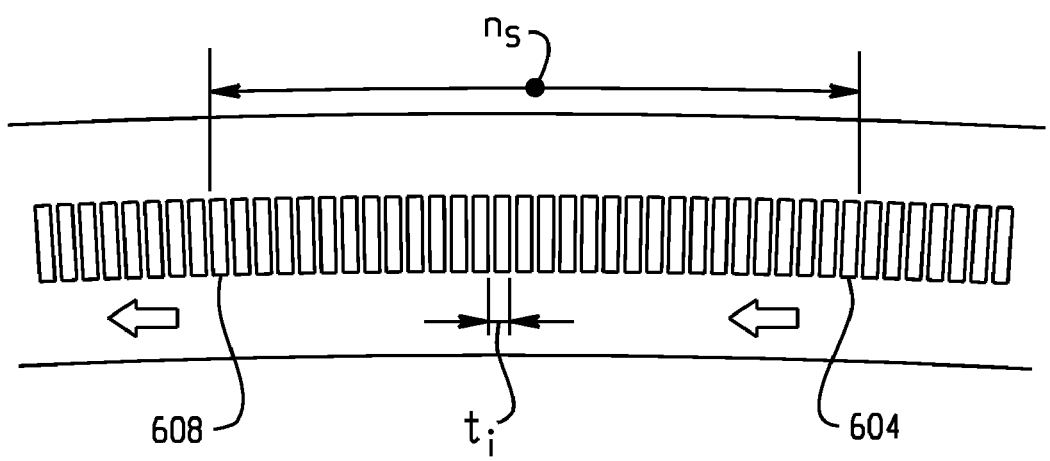
FIG. 6 illustrates another exemplary technique for sweeping the focal spot.

FIG. 6 provides another illustration showing the sweeping of the focal spot during a view. In this example, the electron beam is swept across $n_s$ focal spot positions beginning at the focal spot position 604 and ending at the focal spot position 608. If $t_i$ denotes the time of each focal spot, the total time for one sweep $t_s$ is $n_s t_i$. After a sweep has finished, it restarts again with the same sweep range $n_s$, but advanced by at least one focus position in sweep direction.

In other words, during each sweep the electron beam illuminates $n_s$ focal spot positions in sequence one after another. For the next view, the beam then jumps back to the neighboring focal spot of the first focal spot position of the previous sweep, and sweeps again over $n_s$ spot positions. This pattern repeats for each subsequent view, during which the sweep advances in the sweep direction, and each focal spot position is illuminated $n_s$ times.

In this example, the sweeping of the electron beam across the $n_s$ focal spots is synchronized with the rotation of cathode 116 through each view such that the sweep angle advances one (1) focal spot position after each sweep. The distance between focal spots when the sweep angle advances one (1) focal spot position between sweeps can be expressed in Equation 2.

$$\frac{2\pi r_g}{n} = 2\pi r_g f_g t_s,$$ Equation 2 wherein $r_g$ represents the gantry radius, $f_g$ represents the gantry rotation frequency, $t_s$ represents the total sweep time for one sweep, and n represents the total number of focus positions around the anode 104.

Figure 7:
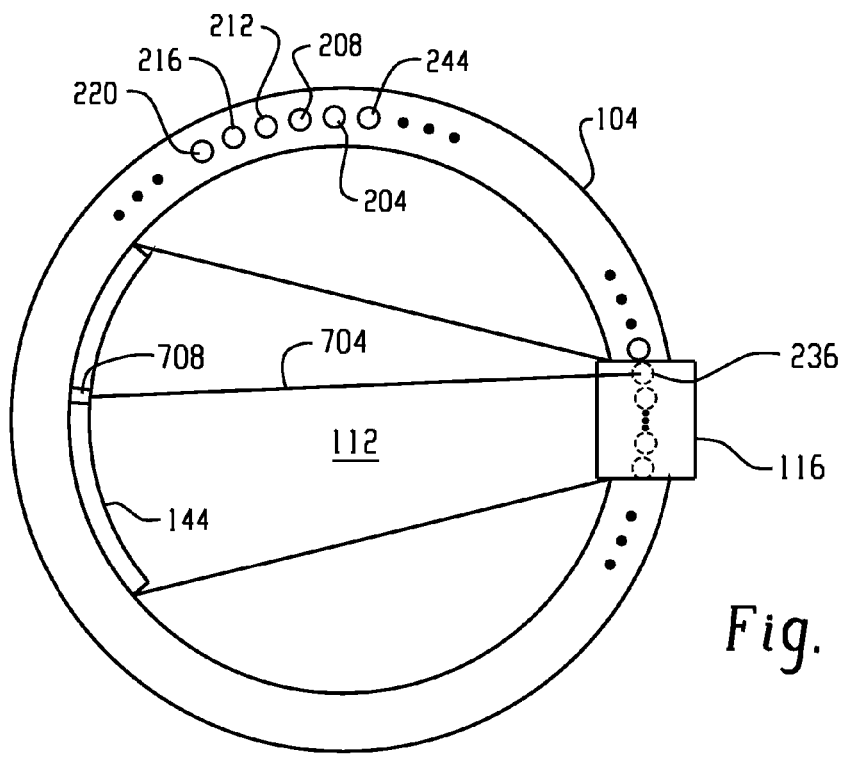
FIGS. 7 and 8 illustrate an exemplary redundant ray path through the examination region.
Figure 8:
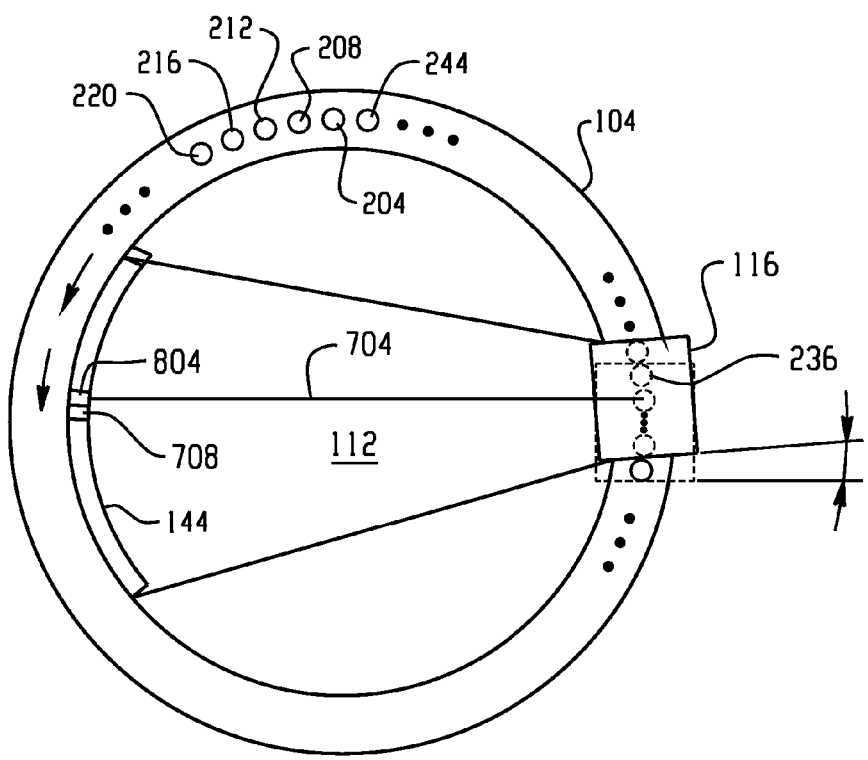

FIGS. 7 and 8 illustrate an exemplary x-ray path from a focal spot that is sampled during multiple views, resulting in redundant samples. FIG. 7 shows an x-ray path 704 from the focal spot location 240, wherein the ray that strikes a detector element 708 during a first view. In FIG. 8, the cathode 116 and the detector array 144 have moved an angular sampling increment of one focal spot position. The illustrated system is configured such that the detector elements are arranged to have the same angular spacing as the focal spots. As a result, the ray emitted from the same focal spot location 236 traverses the same path 704 through the examination region 112, but strikes a detector element 804, which is the detector element adjacent to the detector element 708.

If the detector elements are arranged otherwise, rays traversing similar, but not coincident paths are deemed to have traveled the same path. In one instance, interpolation or the like is used to generate samples along the same path from the samples corresponding to the similar paths.

As a result, a number of redundant rays or x-rays traversing the same path through the examination region 112 are sampled during different views. These redundant rays are combined by the combiner 164 as described in greater detail below.

FIGS. 9, 10, and 11 show examples of suitable combiner 156 configurations for summing each set of redundant rays. In FIG. 9, a plurality of detector elements 904, 908, 912, . . . , and 916 within the detector array 144 count x-rays that traverse the same path through the examination region 112 during different views. In this implementation, the detector elements are photon counting detector elements such as Cadmium Zinc Telluride (CZT) detectors or the like. Each of the detector elements 904-916 provides respective output signal or pulse to a pulse counter 924. Preamplifiers are used to amplify the signals prior to conveying them to the pulse counter 924, if desired.

Digital switches 928 are located in the signal carrying lines between the detector elements 904-916 and the pulse counter 924. Closing a switch 928 establishes an electrical connection between a corresponding one of the detector elements 904-916 and the pulse counter 924. This electrical connection provides a path for the transfer of a signal from a detector element to the pulse counter 924. By closing the switches 928 at an appropriate time, redundant signals corresponding to the same path are conveyed to the pulse counter 924. The pulse counter 924 sums the signals, and the aggregate signal or digital count value is conveyed to the reconstructor 168.

Only one pulse counter 924 is shown in FIG. 9. However, the system 100 includes a plurality of the counters 924. The number of counters 924 employed is a function of the number of focal positions within each sweep angle and the number of detector elements in the detector array 144. For instance, if the number of focal spot positions within a sweep angle is Ns and the number of detector elements in the detector array is Nd, then the total number of counters 924 is the product of the number of focal spot positions within the sweep angle and the number of detector elements in the detector array, or Ns×Nd. A switched matrix of counters 924 is used between the Nd detector elements and the Ns×Nd counters 924 as illustrated in FIG. 10. By combining the data as such, the amount of data conveyed from the detection system to the reconstructor 160 is reduced, which reduces the data pipeline load of the system 100.

FIG. 10 shows an approach similar to that illustrated in FIG. 9, but using crystal/photodiode or direct conversion detector elements 1004, 1008, 1012, . . . , and 1016 to detect redundant rays and produce and provide analog current output. The output of each detector element is conveyed to respective current-to-frequency converters 1024, 1028, 1032, . . . , and 1036. The output of the converters 1024-1036 is conveyed to a pulse counter 1044 through digital switches 1048. Similar to the switches 928, each of the switches 1048 is individually closed at a suitable time to provide an electrical pathway between a corresponding one of the detector elements 1004-1016 and the pulse counter 1044 for signals indicative of redundant rays. The pulse counter 1044 sums these signals and conveys the aggregate signal to the reconstructor 168. Similar to the above approach, only one pulse counter 1044 is shown and a matrix of such counters 1044 are used, wherein one counter 1044 is used for each set of redundant rays.

FIG. 11 show another approach using crystal/photodiode or direct converter detector elements 1104, 1108, 1112, . . . , and 1116. In this configuration, the analog current corresponding to redundant rays from the detector elements 1104-1116 is sent to an analog-to-digital (A/D) converter 1124 through analog switches 1128. The converter 1124 integrates and converts the current. The A/D converter 1124 is a current-to-frequency or other type of converter. The output of the converter 1124 is provided to the reconstructor 168. In this example, only one converter 1124 is shown, but it is to be appreciated that a converter 1124 is provided for each set of redundant rays.

FIG. 12 illustrates a cross section view of an exemplary anode/cathode system. In this example, the stationary anode 104 and the rotating cathode 116 are disposed within a housing 1200. The housing 1200 is ring-shaped with an aperture in which the examination region 112 lies within. The cathode 116 includes a cathode cup 1202 and an emitter 1204 that emits electrons to form an electron beam 1208. The emitter 1204 is a thermal emitter, a cold field emitter, or other type of emitter.

One or more of the steering grid 124, an acceleration grid 1216, and an electrostatic deflection plate 1220 is included to direct the electron beam on the anode 104. As described above, the steering grid 124 pulses the emission of electrons. In the illustrated example, the steering grid 124 toggles the emission of electrons "on" and substantially "off" to generate each pulse. In one instance, this includes invoking the emission of electrons for a first time period, while reducing or stopping the electrons from being emitted during a second time period.

As described above, the focusing and deflection unit 128 sweeps the pulsed electron beam 1208 along the anode 104. In the illustrated rotating cathode implementation, the voltage applied to the cathode cup 1202 is provided via a high voltage slip-ring 1228 or the like. An optional heat dissipation mechanism 1232 cools the anode 104 as the focal spot is being generated. The heat dissipation mechanism includes a cooling medium such water, a liquid metal or the like.

FIG. 13 illustrates a method for scanning with the system 100. The method includes rotating the focal spot around the examination region 108 for one or more views (1304). During each view, the focal spot is also swept along the anode to generate a plurality of focal spots (1308) as described above. The paths from each focal spot to the detectors are sampled for each focal spot during multiple views (1312). Redundant rays corresponding to rays traversing the same or substantially similar paths through the examination region 112 are combined (1316). The resulting data is reconstructed to generate volumetric image data (1320).

Other aspects are presented.

For example, the foregoing discussion has focused on an arrangement in which corresponding focal spots generated in different views have common angular positions. It will be appreciated, however, that the focal spots may offset, for example in one or both of the longitudinal directions. In one such implementation, corresponding focal spots are interleaved among two or more views. One advantage of such an arrangement is that the power dissipation may more uniformly distribute the power dissipation across the surface of the anode.

In the illustrated embodiment, a rotating cathode 120 generates and emits the electron beam that generates the focal spots. In another embodiment, a stationary electron gun or cathode sweeps the electron beam along the anode 104. In yet another embodiment, a plurality of cathode emitters are stationarily distributed around the examination region 108. Each of the emitters is individually addressed or switched to sequentially generate the focal spots along the anode 104.

In another embodiment, the scanner includes two or more electron beams for concurrently generating two or more focal spots that sweep along the stationary annular anode. In one instance, the electron beams are angularly offset about the examination region 108 at the same z-axis location. In another instance, the electron beams are angularly offset at different z-axis locations. In yet another instance, the electron beams are at the same angular position about the examination region 108 and offset along the z-axis.

In another embodiment, the electron beam is continuously swept throughout the sweep distance. Continuous sweeping typically results in a generally more homogenous distribution of the beam energy on the surface of the anode 116. Although some spatial blurring may result, one advantage of such a distribution of the energy is that it may lower the anode base temperature.

In the illustrated system, the detector elements are arranged to have the same angular spacing as the focal spots. In an alternative embodiment, the detector elements are arranged otherwise and rays traversing similar, but not coincident paths are deemed to have traveled the same path. In one instance, the rays deemed similar are combined by the combiner 164 to generate the aggregate signal for each focal spot. In another instance, interpolation or the like is used to generate samples along the same path from the samples deemed to have traveled the same path.

In another implementation, the focal spot additionally or alternatively sweeps along the anode in a longitudinal direction.

In the illustrated embodiment, the data combiner 164 is shown external to the gantry 108. In another embodiment, the data combiner 164 may be located within the gantry 108. In yet another embodiment, the data combiner 164 may be distributed such that a portion of it is located within the gantry 108 and another portion is located external to the gantry 108.

In another embodiment, the anode 104 rotates about the examination region 112. In one instance, the rotating anode is ring-shaped as described herein. In another instance, the rotating anode is an arc or otherwise shaped segment.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A computed tomography method, comprising:
 rotating an electron beam along an anode disposed about an examination region for a plurality of sampling intervals in which x-ray projections are sampled;

sweeping the electron beam during each sampling interval to generate a plurality of successive focal spots at different focal spot locations, wherein the focal spots generated in a given sampling interval include a sub-set of the focal spots generated in a previous sampling interval;

sampling x-ray projections radiated from each of the plurality of focal spots for each sampling interval; and reconstructing the x-ray projections to generate volumetric image data.

2. The method of claim 1, wherein a sampling interval is shifted by at least one focal spot position with respect to a previous sampling interval.

3. The method of claim 1, wherein the electron beam rotates one focal spot position for each sampling interval.

4. The method of claim 1, wherein an x-ray projection path from a focal spot is sampled during more than one sampling interval.

5. The method of claim 4, further including combining the individual samples of the path to generate an aggregate signal for the path.

6. The method of claim 1, wherein the method includes pulsing the electron beam so as to generate a plurality of discrete focal spots.

7. The method of claim 1, wherein the electron beam rotates in coordination with a rotating detector array that samples the x-ray projections.

8. The method of claim 1, wherein the electron beam is generated by a cathode that rotates about a longitudinal axis of the examination region.

9. The system of claim 1, wherein the electron beam is generated by a plurality of emitters distributed around the examination region and next to and offset from the anode.

10. The system of claim 1, wherein the anode is ring-shaped and surrounds the examination region.

11. The system of claim 1, wherein the anode is an arc-shaped segment.

12. The method of claim 1, wherein
the electron beam rotates about a longitudinal axis in a first direction;
the focal spot locations generated in a first sampling interval subtend a first angular range about the longitudinal axis;
the focal spot locations generated in a second, successive sampling interval subtend a second angular range about the longitudinal axis; and
the second angular range is angularly offset from the first angular range in the first direction by a non-zero angular distance which is less than the first angular range.

13. A computed tomography system, comprising:
an anode;
an electron beam source that rotates and sweeps an electron beam along the anode for a plurality of sampling intervals in which x-ray projections are detected, wherein the electron beam is swept during each sampling interval to generate a plurality of focal spots at different focal spot locations and successive sweeps partially overlap;
a detector array that samples x-ray projections radiated from each of the plurality of focal spots that traverse an examination region; and
a reconstructor that reconstructs the x-ray projections to generate volumetric image data.

14. The system of claim 13, wherein the electron beam advances at least one focal spot position during a subsequent sampling interval and the electron beam is swept beginning with a focal spot that was generated in the previous sampling interval.

15. The system of claim 13, wherein the electron beam is swept through a sweep angle during each sampling interval beginning at an initial focal spot position within the sweep angle, and wherein the sweep angle for contiguous sampling intervals includes overlapping focal spots.

16. The system of claim 13, wherein each focal spot is generated and sampled in more than one sampling interval.

17. The system of claim 13, wherein the detector array detects redundant rays for a focal spot by detecting x-rays traversing substantially similar paths through the examination region for a focal spot during different sampling intervals.

18. The system of claim 17, further including a data combiner for each set of redundant rays to combine signals representative of the redundant rays to generate an aggregate signal for each focal spot.

19. The system of claim 13, wherein the electron beam source includes a grid that pulses the electron beam to generate each focal spot.

20. The system of claim 13, wherein the electron beam source includes a deflection unit that magnetically sweeps the electron beam.

21. The system of claim 13, wherein the electron beam source is one of a rotating cathode that rotates along the anode, a stationary cathode that deflects the electron beam along the anode, and a plurality of field emitters disposed adjacent to the anode.

22. The system of claim 13, wherein the detector array rotates in coordination with the electron beam source.

23. A computed tomography system, comprising:
an anode that surrounds an examination region;
a cathode that rotates along the anode and repetitively sweeps an electron beam through a moving sweep window covering a plurality of focal spot locations to repeatedly generate a plurality of focal spots one after another at different focal spot locations as the cathode rotates around the examination region, wherein the moving sweep window moves so that at least one similar focal spot is generated during two consecutive electron beam sweeps;
a detector array that detects x-rays emitted from each focal spot and generates signals indicative thereof;
a combiner that combines signals corresponding to x-rays that traversed a substantially similar path through the examination region; and
a reconstructor that reconstructs the signals to generate volumetric image data.

* * * * *